(12) United States Patent
van der Burg et al.

(10) Patent No.: US 8,597,336 B2
(45) Date of Patent: Dec. 3, 2013

(54) APPARATUS FOR DISCRETE TISSUE ANCHORING FOR SOFT TISSUE REPAIR AND METHOD OF USE

(75) Inventors: Erik van der Burg, Los Gatos, CA (US); Nathaniel Cohen, Los Gatos, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 751 days.

(21) Appl. No.: 11/966,137

(22) Filed: Dec. 28, 2007

(65) Prior Publication Data

US 2009/0171400 A1  Jul. 2, 2009

(51) Int. Cl.
*A61B 17/56* (2006.01)
*A61B 19/00* (2006.01)

(52) U.S. Cl.
USPC ........................................................ 606/300

(58) Field of Classification Search
USPC ............ 606/77, 232, 76, 300–331, 139–145, 606/213, 215
See application file for complete search history.

(56) References Cited

U.S. PATENT DOCUMENTS

| | | |
|---|---|---|
| 1,088,892 A | 3/1914 | Foreman |
| 2,429,675 A | 10/1947 | Eypper |
| 3,845,772 A | 11/1974 | Smith |
| 3,988,007 A | 10/1976 | Freiburger, Jr. |
| 4,750,492 A | 6/1988 | Jacobs |
| 4,870,957 A | 10/1989 | Goble et al. |
| 4,884,572 A | 12/1989 | Bays et al. |
| 4,976,715 A * | 12/1990 | Bays et al. ...................... 606/77 |
| 5,102,414 A | 4/1992 | Kirsch |
| 5,152,790 A | 10/1992 | Rosenberg et al. |
| 5,236,445 A | 8/1993 | Hayhurst et al. |
| 5,268,001 A | 12/1993 | Nicholson et al. |
| 5,429,641 A | 7/1995 | Gotfried |
| 5,480,403 A | 1/1996 | Lee et al. |
| 5,486,197 A | 1/1996 | Le et al. |
| 5,498,265 A | 3/1996 | Asnis et al. |
| 5,527,341 A | 6/1996 | Gogolewski et al. |
| 5,534,011 A | 7/1996 | Greene, Jr. et al. |
| 5,545,180 A | 8/1996 | Le et al. |
| 5,584,835 A | 12/1996 | Greenfield |
| 5,601,557 A | 2/1997 | Hayhurst |
| 5,618,314 A * | 4/1997 | Harwin et al. ............... 606/232 |
| 5,649,931 A | 7/1997 | Bryant et al. |

(Continued)

FOREIGN PATENT DOCUMENTS

EP   1862127      12/2007
WO   2008/011417 A2   1/2008

OTHER PUBLICATIONS

Rockwood C., et al., The Shoulder, Saunders, 2004; 820-821.
Yamaguchi, K., et al., J. Shoulder Elbow Surg., 2001;10:199-203.

(Continued)

*Primary Examiner* — Michael T Schaper
*Assistant Examiner* — Christopher Beccia
(74) *Attorney, Agent, or Firm* — Lerner, David, Littenberg, Krumholz & Mentlik, LLP

(57) ABSTRACT

Disclosed herein are devices and methods for securing soft tissue to a rigid structure such as bone. Various directional anchors that allow for increasing the stability the attachment of soft tissue to bone are described. Also described is a delivery system for use with the directional anchors that allows for open surgical or arthroscopic application of one embodiment of the device. A method for repairing rotator cuff tears is also described.

23 Claims, 12 Drawing Sheets

(56) References Cited

U.S. PATENT DOCUMENTS

| | | | |
|---|---|---|---|
| 5,667,513 A | 9/1997 | Torrie et al. | |
| 5,725,529 A | 3/1998 | Nicholson et al. | |
| 5,782,864 A | 7/1998 | Lizardi | |
| 5,843,127 A | 12/1998 | Li | |
| 5,849,004 A | 12/1998 | Bramlet | |
| 5,906,617 A | 5/1999 | Meislin | |
| 5,957,953 A | 9/1999 | DiPoto et al. | |
| 5,964,764 A | 10/1999 | West, Jr. et al. | |
| 6,039,741 A | 3/2000 | Meislin | |
| 6,077,267 A | 6/2000 | Huene | |
| 6,129,728 A | 10/2000 | Schumacher et al. | |
| 6,139,565 A | 10/2000 | Stone et al. | |
| 6,238,435 B1 | 5/2001 | Meulink et al. | |
| 6,330,845 B1 | 12/2001 | Meulink | |
| 6,485,503 B2* | 11/2002 | Jacobs et al. | 606/215 |
| 6,554,852 B1 | 4/2003 | Oberlander | |
| 6,626,910 B1* | 9/2003 | Hugues | 606/232 |
| 6,641,597 B2 | 11/2003 | Burkhart et al. | |
| 6,666,877 B2 | 12/2003 | Morgan et al. | |
| 6,682,549 B2 | 1/2004 | Bartlett | |
| 6,689,154 B2 | 2/2004 | Bartlett | |
| 6,692,516 B2 | 2/2004 | West, Jr. et al. | |
| 6,770,084 B1* | 8/2004 | Bain et al. | 606/144 |
| 6,884,248 B2 | 4/2005 | Bolduc et al. | |
| 6,887,259 B2 | 5/2005 | Lizardi | |
| 6,893,452 B2 | 5/2005 | Jacobs | |
| 6,923,830 B2 | 8/2005 | Michelson | |
| 6,926,718 B1 | 8/2005 | Michelson | |
| 7,022,129 B2 | 4/2006 | Overaker et al. | |
| 7,037,324 B2 | 5/2006 | Martinek | |
| 7,081,126 B2 | 7/2006 | McDevitt et al. | |
| 7,083,638 B2 | 8/2006 | Foerster | |
| 7,090,690 B2 | 8/2006 | Foerster et al. | |
| 7,235,100 B2 | 6/2007 | Martinek | |
| 7,309,346 B2 | 12/2007 | Martinek | |
| 7,381,213 B2 | 6/2008 | Lizardi | |
| 7,416,556 B2 | 8/2008 | Jackson | |
| 7,959,649 B2 | 6/2011 | Burkhart | |
| 2002/0161401 A1 | 10/2002 | Steiner | |
| 2002/0169478 A1 | 11/2002 | Schwartz et al. | |
| 2003/0004545 A1 | 1/2003 | Burkhart et al. | |
| 2003/0120309 A1 | 6/2003 | Colleran et al. | |
| 2003/0229361 A1 | 12/2003 | Jackson | |
| 2003/0233100 A1 | 12/2003 | Santarella et al. | |
| 2004/0138706 A1 | 7/2004 | Abrams et al. | |
| 2004/0220574 A1* | 11/2004 | Pelo et al. | 606/73 |
| 2005/0081339 A1 | 4/2005 | Sakabayashi | |
| 2005/0090827 A1 | 4/2005 | Gedebou | |
| 2005/0090862 A1 | 4/2005 | McDevitt et al. | |
| 2005/0192577 A1 | 9/2005 | Mosca et al. | |
| 2005/0240222 A1 | 10/2005 | Shipp | |
| 2005/0267478 A1 | 12/2005 | Corradi et al. | |
| 2006/0004364 A1 | 1/2006 | Green et al. | |
| 2006/0100630 A1* | 5/2006 | West, Jr. | 606/73 |
| 2006/0135996 A1 | 6/2006 | Schwartz et al. | |
| 2006/0200199 A1 | 9/2006 | Bonutti et al. | |
| 2006/0201519 A1 | 9/2006 | Frazier et al. | |
| 2006/0271105 A1 | 11/2006 | Foerster et al. | |
| 2007/0005068 A1 | 1/2007 | Sklar | |
| 2007/0038221 A1 | 2/2007 | Fine et al. | |
| 2007/0043378 A1 | 2/2007 | Kumar et al. | |
| 2007/0156176 A1 | 7/2007 | Fanton et al. | |
| 2007/0167950 A1 | 7/2007 | Tauro et al. | |
| 2007/0250064 A1 | 10/2007 | Darois et al. | |
| 2007/0260259 A1 | 11/2007 | Fanton et al. | |
| 2007/0276412 A1 | 11/2007 | Catanese et al. | |
| 2008/0009904 A1 | 1/2008 | Bourque et al. | |
| 2008/0021474 A1 | 1/2008 | Bonutti et al. | |
| 2008/0033486 A1 | 2/2008 | Whittaker et al. | |
| 2008/0086138 A1 | 4/2008 | Stone et al. | |
| 2008/0140118 A1 | 6/2008 | Martinek | |
| 2009/0043337 A1 | 2/2009 | Martin | |
| 2010/0094355 A1 | 4/2010 | Trenhaile | |
| 2010/0100127 A1 | 4/2010 | Trenhaile | |
| 2011/0245869 A1 | 10/2011 | Burkhart | |

OTHER PUBLICATIONS

Bishop J., et al. Cuff integrity after arthroscopic versus open rotator cuff repair: A prospective study, J. Shoulder Elbow Surg., 2006;15:290-299.

Galatz, L., et al., The outcome and repair integrity of completely arthroscopically repaired large and massive rotator cuff tears, J. Bone Joint Surg. Am., 2004;86A:219-24.

Cumins, C.A., et al., Mode of failure for rotator cuff repair with suture anchors identified at revision surgery, J. Shoulder Elbow Surg., 2003 Mar.-Apr.;12(2):128-33.

Burkhart, S.S., et al., A stepwise approach to arthroscopic rotator cuff repair based on biomechanical principles, Arthroscopy, Jan.-Feb. 2000; 16(1):82-90.

Kim, D., et al., Biomechanical comparison of a single-row versus double row suture anchor technique for rotator cuff repair, Am. J. Sports Med., 2006; 34;407.

U.S. Appl. No. 12/206,643.

U.S. Appl. No. 12/269,256.

U.S. Appl. No. 60/954,558, filed Aug. 7, 2007, entitled Suture-Retaining Device and Anchor.

Partial European Search Report, EP 09169742, dated Jan. 8, 2010.

Partial European Search Report, EP 09175847, dated Feb. 23, 2010.

European Search Report, EP10164525, dated Aug. 6, 2010.

* cited by examiner

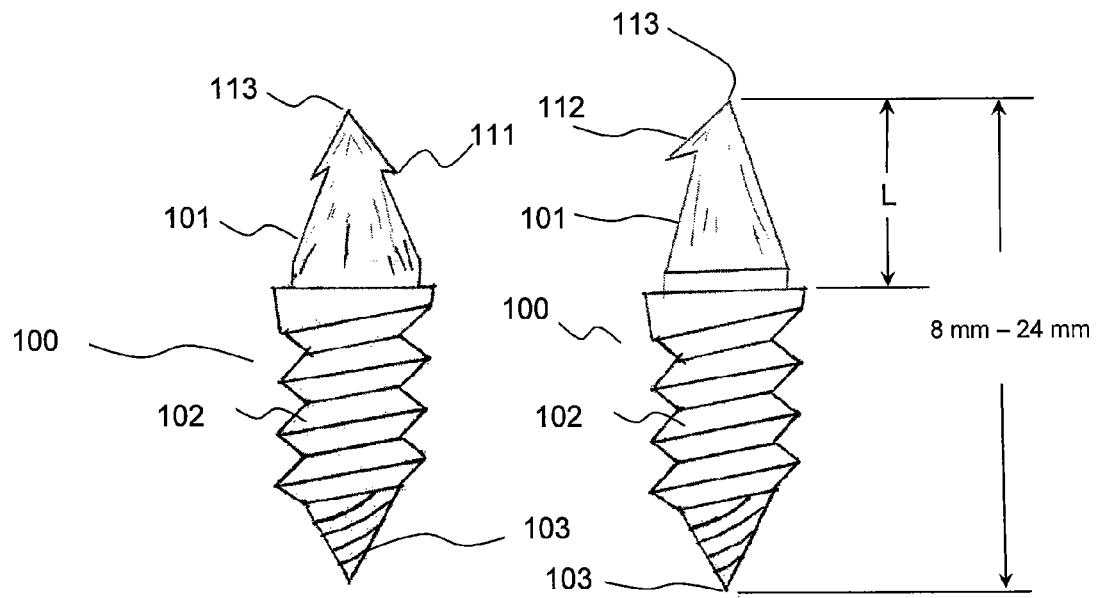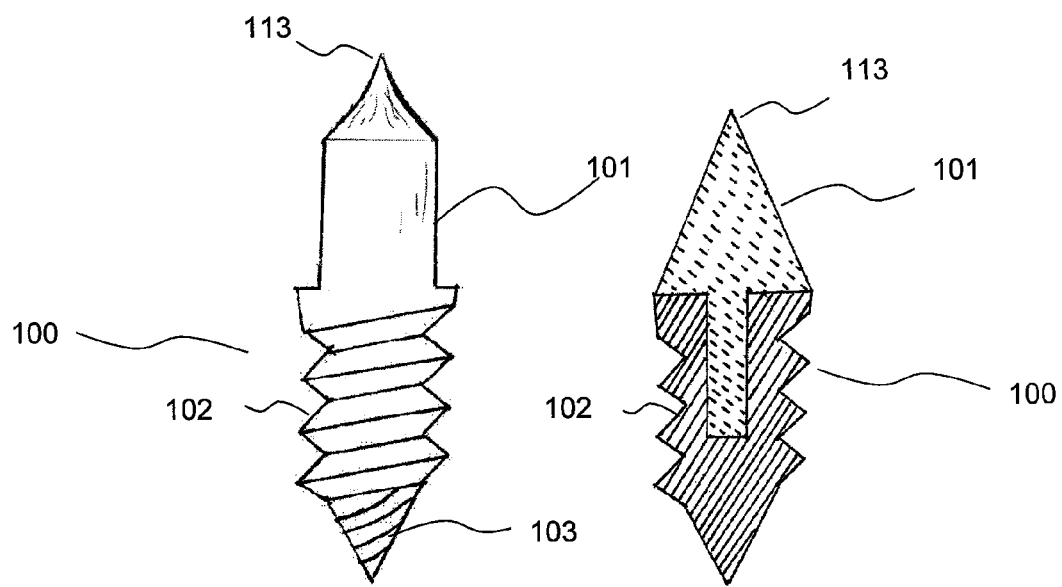
FIG. 1A  FIG. 1B
FIG. 1C  FIG. 1D

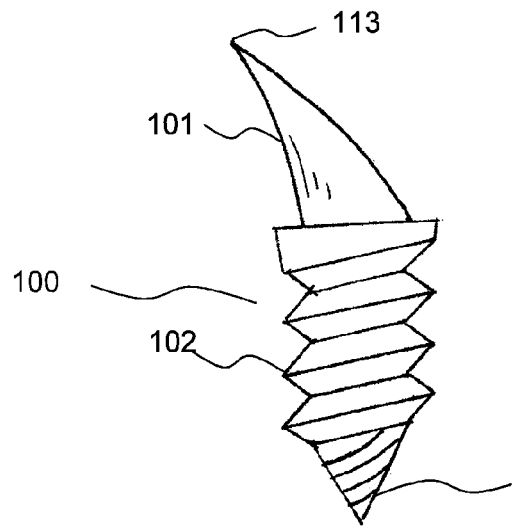
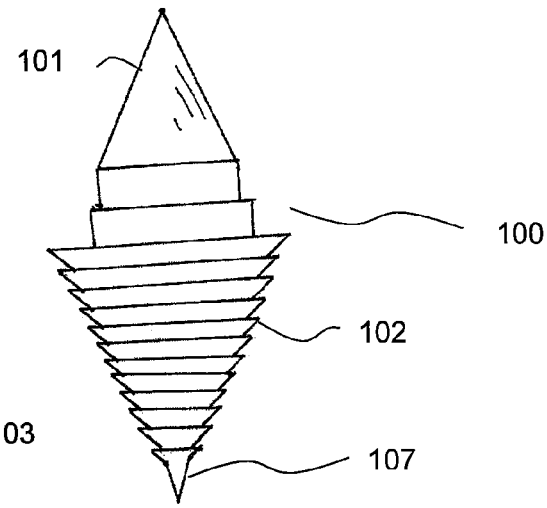
FIG. 1E    FIG. 1F
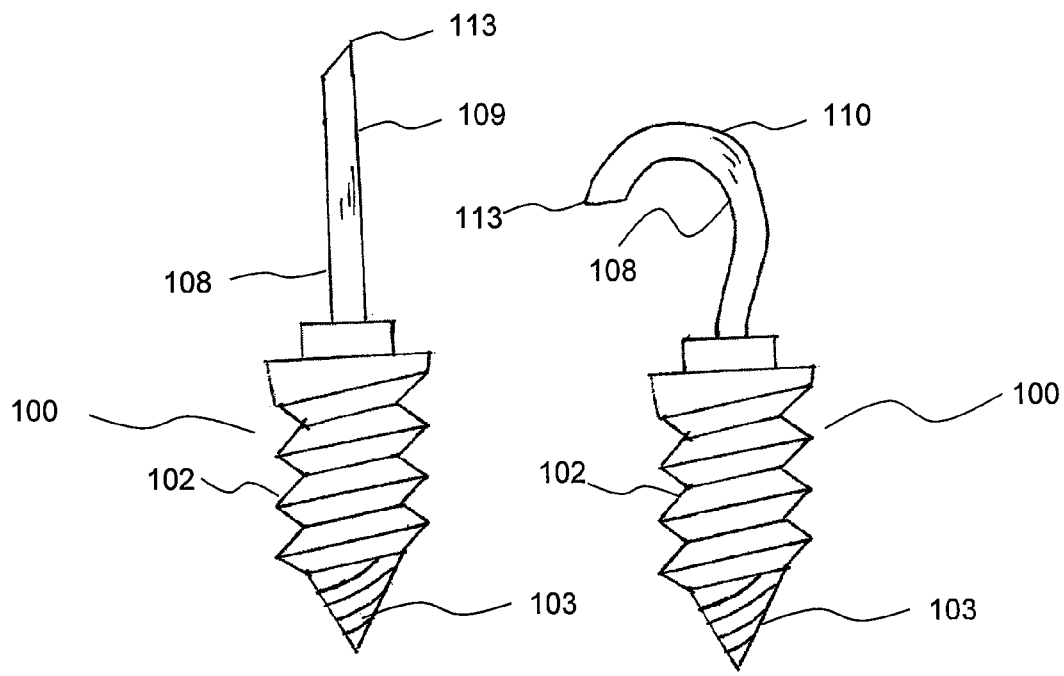
FIG. 1G    FIG. 1H

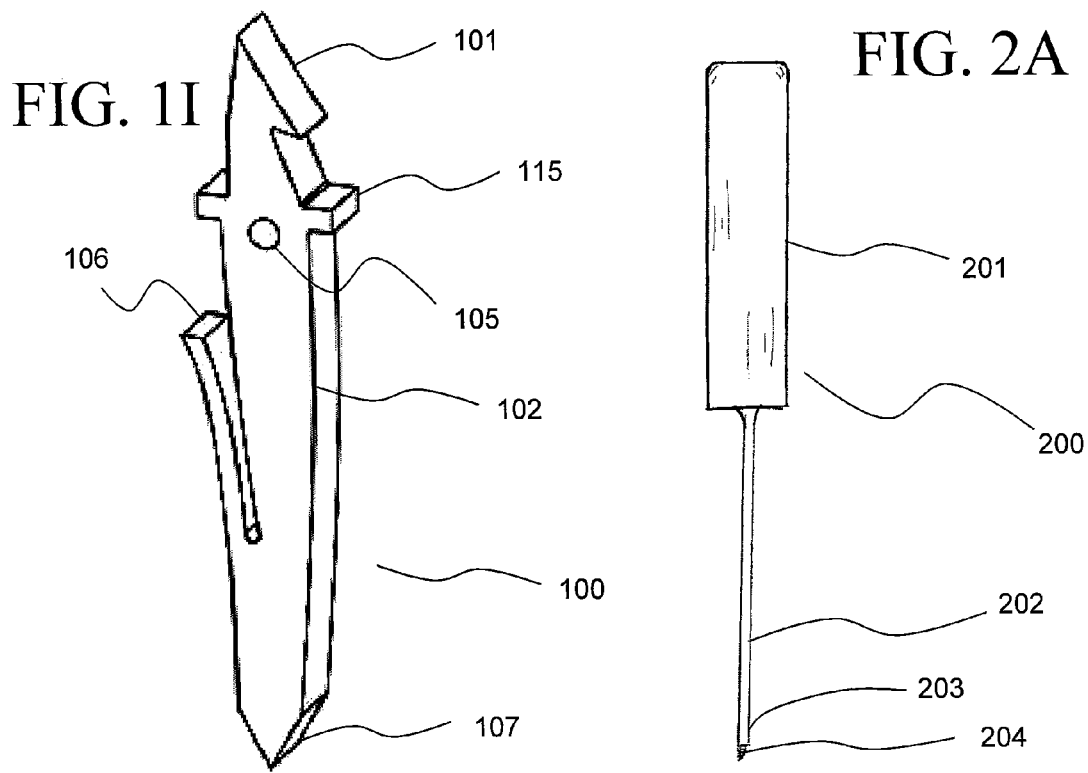
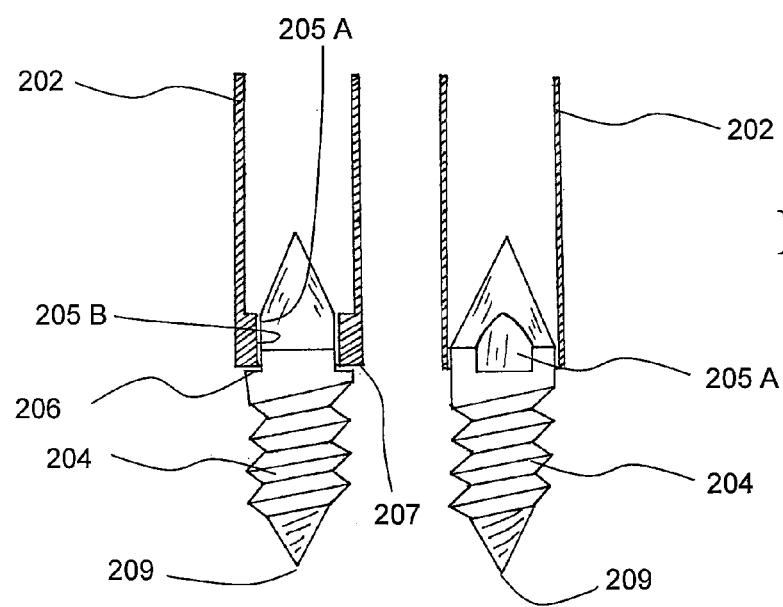

APPARATUS FOR DISCRETE TISSUE ANCHORING FOR SOFT TISSUE REPAIR AND METHOD OF USE

FIELD OF THE INVENTION

The present invention relates to medical devices and procedures. More particularly, the present invention relates to methods and devices for approximation of soft tissue to a rigid material such as bone.

BACKGROUND OF THE INVENTION

There are many medical procedures where a surgeon needs to attach soft tissue to bone. The soft tissue can be tendon or other connective tissue. One very common example of this is rotator cuff repair where a portion or all of the rotator cuff is torn or detached from the humerus. When the rotator cuff tears from the humerus, the result is pain and loss of function. Rotator cuff disease affects a large number of people worldwide, affecting many people over the age of forty. Some studies have shown a prevalence of approximately 30% in people over the age of forty (Rockwood C., et al., *The Shoulder*, Saunders, 2004; 820-821). It is estimated that as many as 17 million people in the United States may be at risk for pain and dysfunction as a result of rotator cuff injuries. While the majority of people are asymptomatic, a significant subset goes on to have disability. One study in patients with rotator cuff tears in one shoulder found that 50% of these patients who had an asymptomatic rotator cuff tear in the other shoulder went on to become symptomatic (Yamaguchi, K., et al., *J. Shoulder Elbow Surg.*, 2001; 10:199-203).

The prevalence of symptomatic rotator cuff disease is reflected in the large numbers of surgical repair for this condition. Rotator cuff repair is one of the most common orthopedic procedures performed. When a patient presents with a significant rotator cuff tear, surgical repair is performed. The goal of surgical repair of the rotator cuff is to secure the tendon to the bone in a stabile manner so that the tendon and bone can heal. If the tendon is not stabile and oscillation or micro-motion between the tendon and bone develops, the healing process will be interrupted. In this situation, it is less likely that the tendon will heal properly to the bone, resulting in a re-tear. Thus, the more stable the repair, the more successfully the tendon will heal to the bone.

Rotator cuff repair is performed open or arthroscopically, most often using suture anchors. These have one point of fixation with either one suture or several sutures attached for attaching the tendon to the bone. While arthroscopic repair is less painful and thus more attractive to patients, many surgeons continue to perform open rotator cuff repairs. Much of the reason for this is due to the challenge of arthroscopic shoulder surgery. There is a significant learning curve in gaining the skills to be able to manage multiple strands of suture in a relatively small field of view, passing these through the tendon and tying them down. Many of theses techniques can be relatively time-consuming when compared with open surgery.

There is a growing body of literature showing that surgical rotator cuff repair has a high rate of failure. Failure of rotator cuff repairs is a well-described complication of rotator cuff repairs, both open and arthroscopic. For example, Gerber et al. found a re-tear rate of 20% following isolated repair of the supraspinatus Fuchs found a re-tear rate of 20% following isolated repair of the supraspinatus (Fuchs B, et al., *Clinical and structural results of open repair of an isolated one-tendon tear of the rotator cuff, J Bone Joint Surg Am.*, 2006 Febuary; 88(2):309-16). Liem found a re-tear rate of 31.6% in arthroscopic supraspinatus and 36.8% in patients undergoing mini-open repair (Liem D., et. al., *Arthroscopy*, 2007 May; 23(5):514-21). Galatz found an even higher re-tear rate in larger tears (Galatz, L., et al., *The outcome and repair integrity of completely arthroscopically repaired large and massive rotator cuff tears, J. Bone Joint Surg. Am.*, 2004; 86A: 219-24). Tendon-to-bone reattachment in a rotator cuff repair procedure can fail by a number of means. In a review of failed rotator cuff surgeries evaluated at re-operation, Cummins cited as one of the weak links in the repair, the suture-tendon interface (Cumins, C.A., et al., *Mode of failure for rotator cuff repair with suture anchors identified at revision surgery, J. Shoulder Elbow Surg.*, 2003 March-April; 12(2):128-33). To reduce the load on any one suture, (i.e., greater distribution of loads) suture anchors used in tendon repair have begun to add multiple sutures to each suture anchor. Burkhart illustrates that the load on each suture diminishes as the number of sutures holding the tendon in place increases (Burkhart, S. S., et al., *A stepwise approach to arthroscopic rotator cuff repair based on biomechanical principles, Arthroscopy*, 2000 January-Febuary; 16(1):82-90). Kim demonstrated less strain and greater tendon-bone stability in repairs made with multi row (4 fixation points) than with single row (2 fixation points). However, even in the repairs made with 4 fixation points, slippage (oscillation and micro-motion) between the tendon and bone was greater than 3.0 mm after just 200 cycles of physiological loading (Kim, D., et al., *Biomechanical comparison of a single-row versus double row suture anchor technique for rotator cuff repair, Am. J. Sports Med.*, 2006; 34; 407).

With current suture anchor based fixation techniques, it is difficult to get more than four points of fixation, particularly in arthroscopic repair, for two reasons. First, the challenge and time required to manage multiple sutures can greatly lengthen procedure time and complexity. Second, suture anchors commonly use a 5.0 mm diameter anchor that is anchored into bone. The typical footprint size (area that the tendon connects to the bone) for the supraspinatus tendon is 25 mm long and 15 mm wide. Placement of more than a few 5.0 mm diameter anchors into this area may significantly compromise the strength of the bone as well as disrupt the very bone that the tendon needs to heal to.

The concept of distributing physiological loads over multiple fixation points in tissue repair has been previously described by Jacobs (U.S. Pat. No. 6,893,452). Jacobs describes approximating soft tissue with a planar structure that contains multiple fixation points integrated onto it. Use of such a system in attaching tendon to bone would cover a significant percentage of the bone that the tendon needs to heal to and therefore may not be a desirable method for repairing tendon to bone.

Thus what is needed is a tendon to bone fixation method and device that will enhance the stability of the tendon to bone interface which in turn will minimize gap formation and tendon/bone micro-motion and provide a greater opportunity for the tendon and bone to heal properly. The ideal method and device would not require the use of additional sutures, but possibly reduce the number of sutures required to adequately stabilize the tendon to the bone, thus simplifying the procedure.

SUMMARY OF THE INVENTION

The present invention solves the difficulty with adequately stabilizing soft tissue to bone in soft tissue repair by providing multiple discrete points of fixation that allow for improved distribution of loads and a more stable tissue to bone interface. In particular, one or more directional anchors are implanted in bone and have tissue anchoring elements that pierce or engage tissue, such as a tendon, in order to repair a rotator cuff as an example. The directional anchors attach and stabilize the tendon to the bone and resist directional forces acting to pull the tendon away from or along the bone. The present invention does not require the need for greater numbers of sutures, which make repair more difficult, or other structures that may limit the ability of the soft tissue to heal to bone. Current techniques for attaching tendon to bone require the use of sutures and suture anchors which, due to their size and difficulty in management, limit the number of fixation points reasonably achievable and therefore limit the degree of stability that can be achieved during repair. The present invention discloses devices and methods for more securely stabilizing the tendon to the bone without the need for additional sutures, suture anchors, or other structures that may limit the ability of the tendon to heal to the bone.

BRIEF DESCRIPTION OF THE DRAWINGS

FIGS. 1A-1C depict various discrete tissue to bone directional anchors.

FIG. 1D depicts a multi-component discrete tissue to bone directional anchor.

FIG. 1E depicts a threaded tissue to bone directional anchor with an asymmetric tissue anchor.

FIG. 1F depicts a barbed tissue to bone directional anchor with a symmetric tissue anchor.

FIGS. 1G and 1H depict a tissue to bone directional anchor with a shape changing tissue-anchoring element.

FIG. 1I depicts a tissue to bone directional anchor which can also function as a suture anchor.

FIGS. 2A and 2B depict a delivery tool for the tissue to bone directional anchors shown in FIGS. 1A-1H.

DETAILED DESCRIPTION OF THE PREFERRED EMBODIMENTS

Figure 3A:
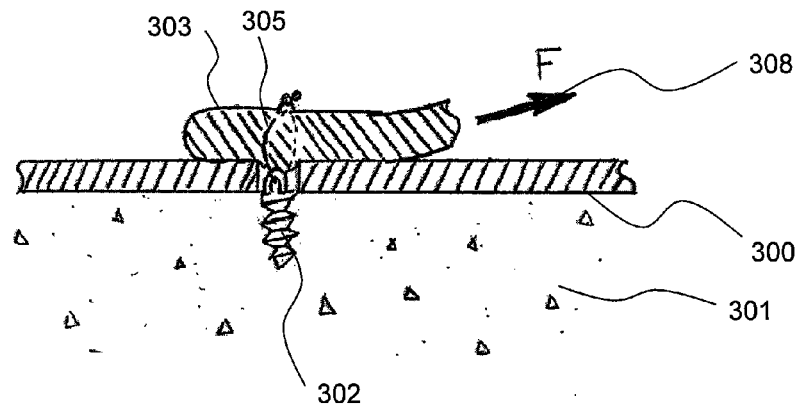
FIGS. 3A-3C depict gap formation with prior art tissue to bone anchoring techniques and with discrete tissue to bone directional anchors.

Several embodiments of the device of this invention are shown in FIGS. 1A-1F. Each of these devices, hereinafter called directional anchors 100, contains a bone-anchoring element 102 that is designed to anchor to bone and a tissue-anchoring element 101 that is designed to anchor to soft tissue. The directional anchors may also have self-tapping 103 or piercing 107 features that facilitate implantation into a hard object or bone. The bone-anchoring element 102 ideally has features such as threads, barbs or other anchoring features as shown in FIGS. 1A-1H, that would enable the surgeon to simply and stably anchor the directional anchor 100 into bone. Other techniques for anchoring structures into bone have been previously described and could be incorporated with this invention. The tissue-anchoring element 101 may have features, as shown in FIGS. 1A and 1B, such as barbs 111 and hooks 112, which enable better anchoring to soft tissue than prior art devices. The tissue-anchoring element 101 generally has a pointed tip 113 to facilitate penetration and engagement with soft tissue and the barb 111 functions to resist detachment of the tissue from the tissue-anchoring element. It may be desirable to have one, multiple or all elements of the directional anchors bioresorbable. FIG. 1D depicts a directional anchor 100 constructed from multiple materials. In one embodiment, the tissue-anchoring element 101 could be made from a bioresorbable or biodegradable polymer and the bone-anchoring element 102 could be made from a non-bioresorbable or non-biodegradable material such as titanium, stainless steel, nickel-titanium alloy (nitinol), PEEK or other suitable material commonly used in orthopedic implants. Polymers synthesized from monomers comprising esters, anhydrides, orthoesters, and amides are particularly suitable for biodegradation. Examples of biodegradable polymers are polyglycolide, polylactide, poly-α-caprolactone, plydiaxanone, polyglyconate, polylactide-co-glycolide, and block and random copolymers of these polymers.

As shown in FIGS. 1G and 1H, a tissue-anchoring element 108 may be made from a material that allows for changing from a tissue-piercing configuration 109 to a tissue-engaging configuration 110. This change in configuration may take place with external forces or from shape-memory or super-elastic recovery of the tissue-anchoring element 108 from the tissue-piercing configuration to the tissue-engaging configuration. Nickel titanium alloy (nitinol) is one example of a material with both shape-memory and super-elastic properties.

FIG. 1I illustrates one embodiment of the present invention that is constructed with features that allow for the directional anchor to also function as a suture anchor. In this particular embodiment, a through hole 105 designed to accommodate sutures of various sizes is placed into the bone anchoring portion of the device 102. With this embodiment, as can be seen in FIG. 3E, the suture anchoring portion of the embodiment can be used in a similar fashion to current suture anchors to hold the tissue to the bone, and the tissue anchor 101 will further stabilize the tissue to prevent slippage of the tissue along the bone. One or multiple rigid tissue anchoring elements 101 may be incorporated in this embodiment. The particular embodiment shown in FIG. 1I incorporates the protrusions 115 which facilitate implantation of the directional anchor to the proper depth. As these features come in contact with the bone, a significant increase in force, which can be felt by the surgeon, is required to further advance the bone anchoring portion 102 into bone. The cantilevered element 106 on this device provides resistance to pullout. The element 106 will bend towards the center of the directional anchor during implantation into bone creating a relatively low profile. As forces are applied to pull the directional anchor out of the bone, the element 106 will engage with bone and be pulled away from the midpoint of the directional anchor, thus creating a larger profile and requiring greater pull out force.

Importantly, with respect to all of the embodiments of the directional anchor 100 shown in FIGS. 1A-1I, the tissue anchoring element 101 (or 108) penetrates only one surface of the tendon (or tissue) and does not go all the way through the tendon like the prior art sutures. It is possible that the tissue anchoring element 108 shown in FIGS. 1G and 1H will penetrate both surfaces of the tendon (or tissue) as the element undergoes a phase transformation and bends through the tendon. While not desired, it is also possible that the overall length of the tissue engaging elements are longer than the thickness of the tendon being repaired, resulting in the upper surface (away from the bone) being penetrated. Further, since the directional anchors 100 are implanted directionally at an angle opposite to the force vectors pulling on the tendon, the tissue anchoring elements 101 actually pull the tendon down onto the bone which promotes healing. While it is preferred that the directional anchors 100 be implanted at an angle opposite to the forces pulling on the tissue/tendon, some benefit may be derived from directional anchors positioned 90° to such forces, or even angles in the same direction as such forces. For example, if the directional anchors 100 have a barb 111 or hook 112 (see FIGS. 1A and 1B), it is possible for the anchors to be implanted at an angle of 90° to the force vector on the tissue or tendon or even angled in the same direction because the hooks/barbs will grab onto and hold the tissue/tendon onto the bone.

FIGS. 2A and 2B depict a delivery system for one embodiment of the invention. As shown in FIG. 2A, an insertion tool 200 has a handle 201 and an elongated shaft 202 that has a distal end 203 opposite the handle. The distal end of the elongated shaft is configured to releasably attach to the directional anchor 204 in a way that allows for the application of torque between the insertion handle and force in the distal direction. The planar interface 205A on the directional anchor 204 and the planar surface 205B on the shaft 202 matingly engage to allow for the transmission of torque between the shaft and the directional anchor. As the handle is rotated clockwise, the planar surfaces 205A and 205B matingly engage to provide clockwise rotation of the directional anchor 204 into bone. The interference between a relief surface 206 on the directional anchor 204 and a flange surface 207 on the distal end of the shaft 202 allows for transmission of distally directed force from the shaft to the directional anchor. With distally directed force and the application of torque, the surgeon can drive the directional anchor point 209 into a hard surface such as bone. The configuration of the surfaces 205A, 205B, 206 and 207 also provide longitudinal stability between the shaft and directional anchor 204. Standard screw heads would not be optimal in engaging bone with the directional anchor due to the features on the tissue anchoring element and the need to be able to place the directional anchors through an arthroscopic cannula.

Alternative configurations for implanting the directional anchor 204 into bone can be used. These may include snap fits, threaded connections, or press fits between the delivery system shaft and the directional anchor. The delivery system may also have additional components in the shaft such as push rods to forcibly impact the directional anchor into bone. Another embodiment may be configured to completely contain the directional anchor within a shaft that is configured to pierce tissue and approximate bone at which point the directional anchor could be screwed, impacted or otherwise connected to bone.

FIG. 3A illustrates a common prior art configuration for attaching tendon to bone. A suture anchor 302 with a pre-attached suture 305 is first driven into the cortical shell 300 and then the cancellous portion 301 of bone, after which one or both of the ends of the suture line 305 are threaded through tendon 303. The two ends of the suture line 305 are then connected with any one of a variety of knot types to bring the tendon 303 in direct contact with the bone. In tendon repair, it is a common practice to mechanically abrade or shave the cortical shell to achieve a bleeding surface. It is believed that a bleeding surface will promote more rapid healing of the tendon to the bone. Stable apposition between the tendon and bone will promote healing while micro-motion or oscillation between the tendon and the bone may disrupt the healing of the tendon to the bone. In current tendon repair techniques, stability between the tendon and the bone largely comes from the compression the suture can apply between the tendon and bone.

Figure 3B:
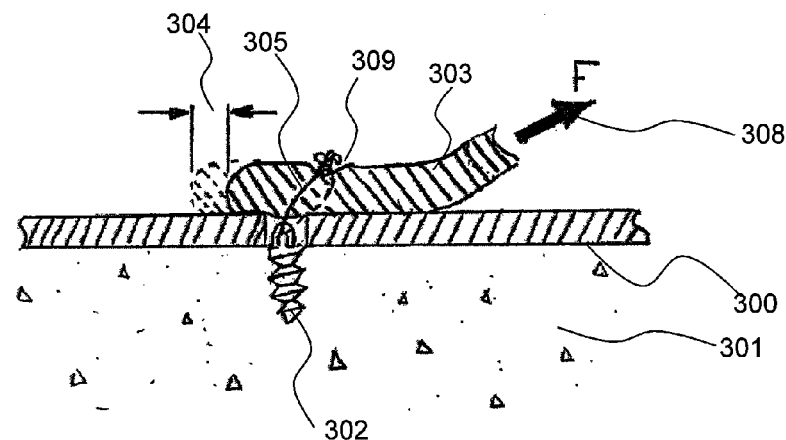

The objective with tendon repair is for the connection between the tendon and bone to remain stable when physiological force F 308 is applied. FIG. 3B depicts how a gap 304 may form when physiological force F 308 is applied to the tendon 303 when only sutures are used to secure the tendon to the bone. As the force F 308 exceeds the frictional forces between the tendon and bone, the tendon slips along the interface between the tendon and the bone and causes flexible, non-rigid suture 305 to further compress the tendon and rotate in the direction of the applied force F until a new force equilibrium is achieved. Thus, the undesired oscillation that results in gap 304 is formed.

Figure 3C:
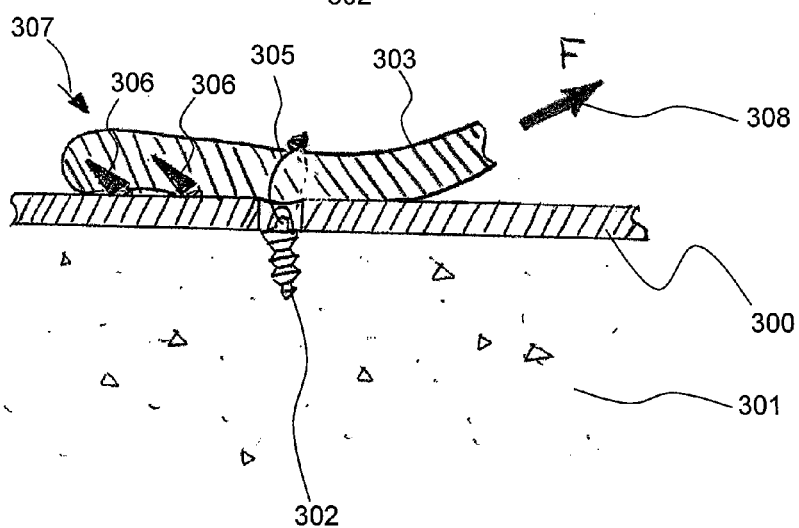

FIG. 3C illustrates one embodiment of the present invention where the stability of the tendon 303 attachment to the bone is augmented with directional anchors 306. In the configuration shown in FIG. 3C, as the physiological force F 308 exceeds the frictional forces between the tendon and the bone, oscillation, micro-motion and gap formation will be limited or prevented because engagement between the tendon and the non-bendable, rigid directional anchors 306 will prevent relative movement between the tendon 303 and bone.

FIG. 3C illustrates one embodiment of the present invention where the directional anchors 306 are inserted into the bone at an angle. The angle between the bone surface and the longitudinal axis of the directional anchor 306 ranges from about 15° to about 87°. Although not a requirement of the invention, the angle as shown would tend to enhance apposition and compressive forces between the tendon and the bone in the direction 307 shown as the force F 308 exceeded the frictional forces between the tendon 303 and bone. One benefit of the current invention is the ability to optimize the position and angle of insertion of each of the directional anchors 306 to resist physiological loads that may vary in direction on a particular tendon, such as a rotator cuff tendon on a shoulder where rotational shear may occur. Another benefit of this embodiment is the preservation of the bone surface for tendon to bone healing. If the tissue anchoring elements were to be mounted onto a planar backing (not shown), some portion of the bone would be covered by the backing, thus interfering with the healing. Additionally, a backing would not necessarily conform to the potentially irregular shape of the bone surface where the tendon needs to heal, such as the greater tuberosity in rotator cuff repair, thus creating a separation between the tendon and the bone in areas of non-contact. With the current embodiment, the natural shape of the bone is preserved and the tendon can maintain optimal contact.

Figure 3D:
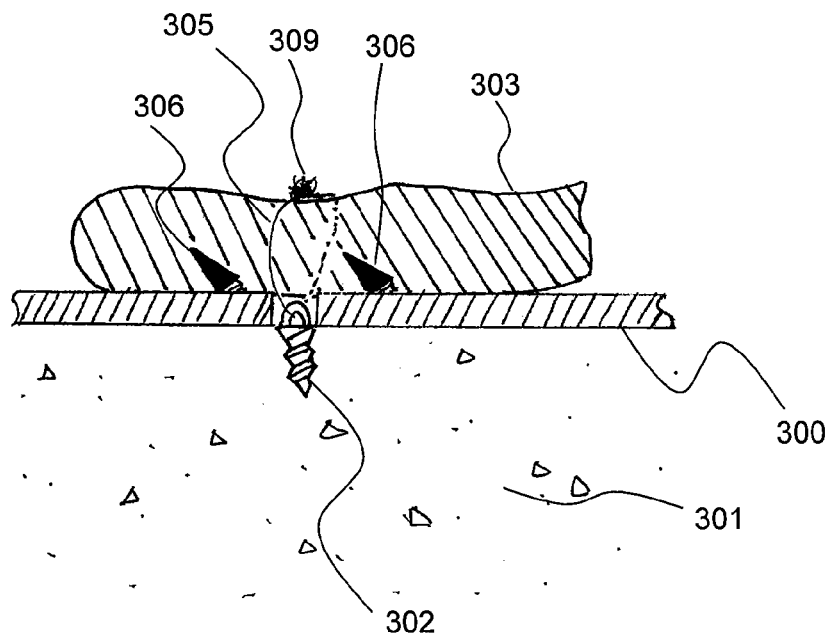
FIGS. 3D-3E depict tissue to bone directional anchors used in conjunction with traditional suture anchors.
Figure 3E:
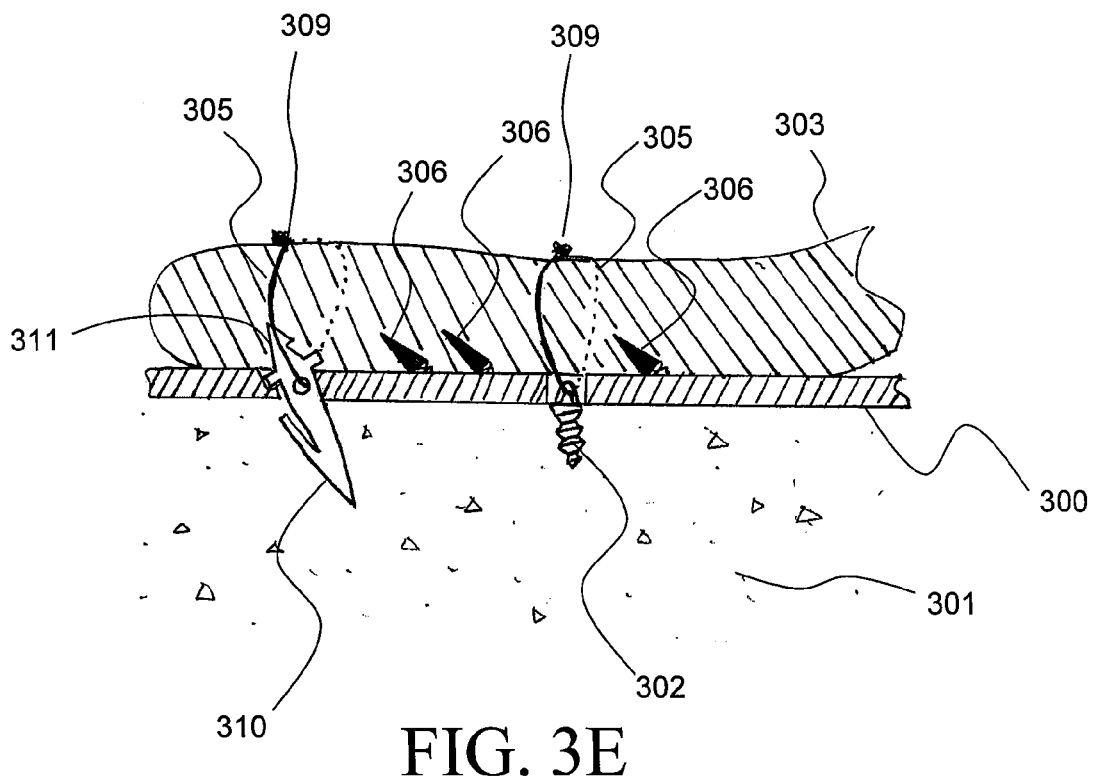

Although FIG. 3C shows one configuration for the directional anchors and suture, the placement of the directional anchors relative to the suture anchor points can vary depending on the anatomy and desired result. For instance, the directional anchors 306 might be placed on one side or both sides of the suture anchor as shown in FIGS. 3D and 3E. FIG. 3E depicts the use of multiple embodiments of the current invention. The directional anchor 310 that includes suture anchoring features is shown stabilizing tissue to the bone with both suture and with the tissue anchor portion 311 of the directional anchor 306. Combining these two elements in one device allows for enhancing tissue stability over the stability that can be achieved with a suture anchor alone. Embodiments of the invention may also be used with non-suture based attachment techniques such as staples or adhesives or used alone to provide all of the tissue anchoring necessary, independent of any other means of attaching tissue to bone.

Figure 4A:
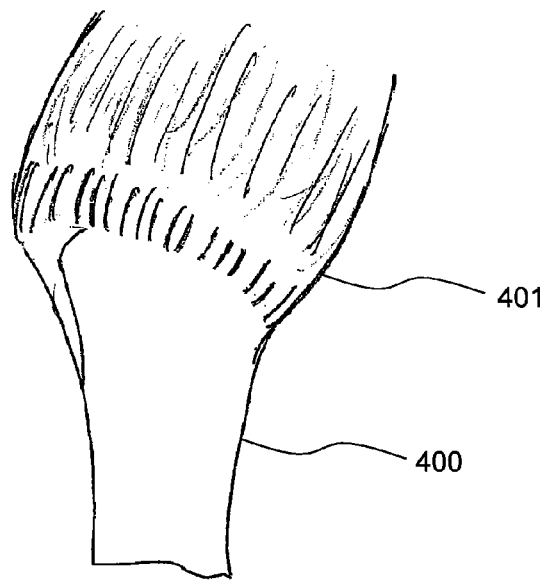
FIGS. 4A-4H depict the various steps of one method for repairing a rotator cuff tendon with discrete tissue to bone directional anchors.
Figure 4B:
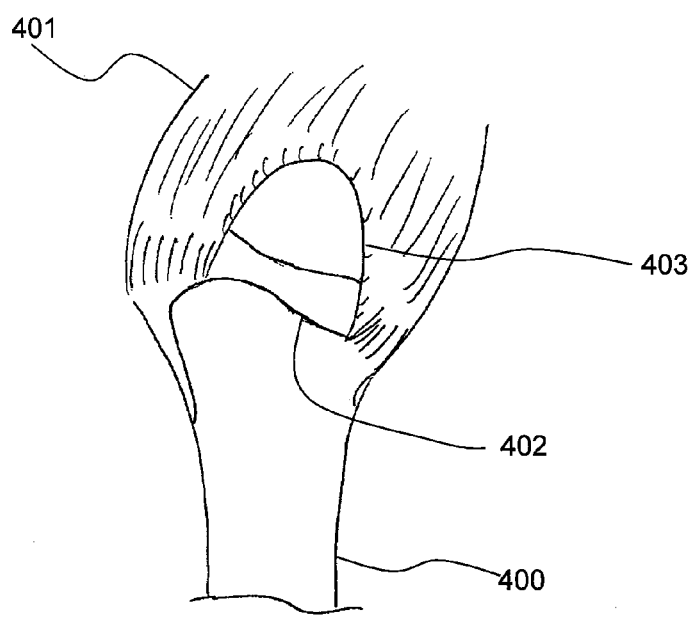
Figure 4C:
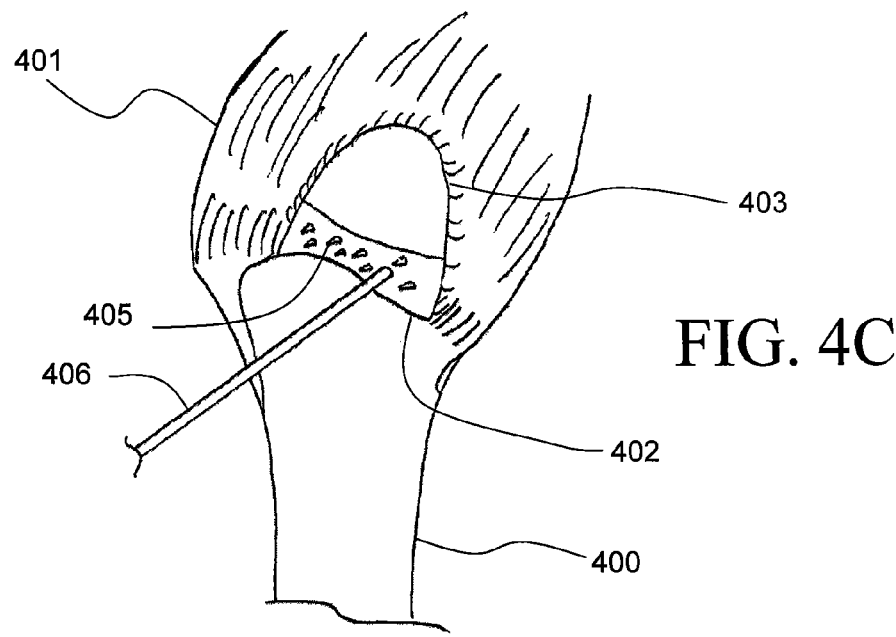
Figure 4D:
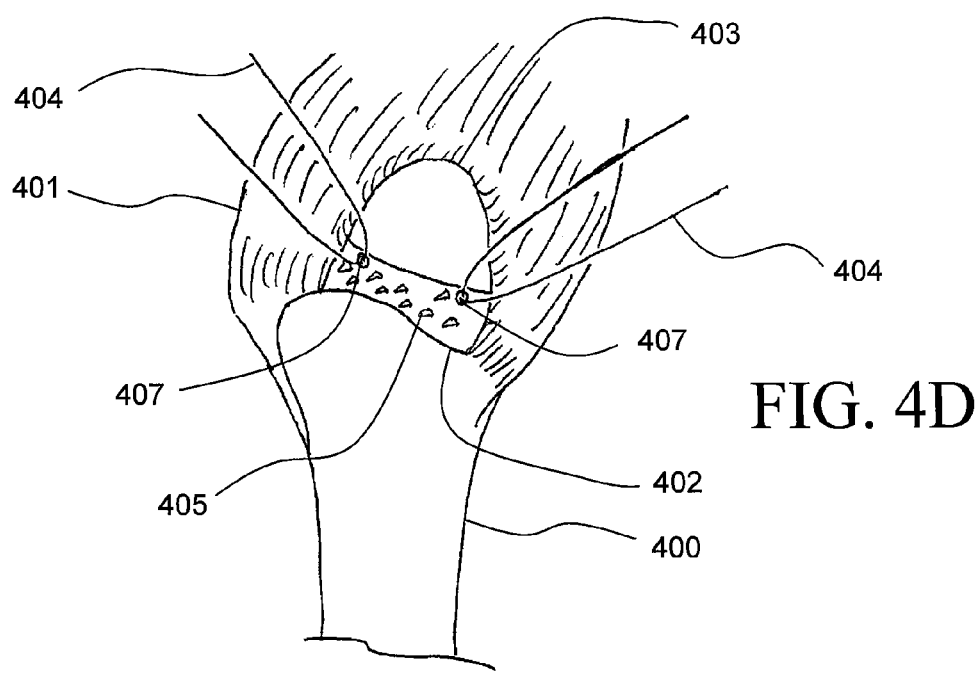
Figure 4E:
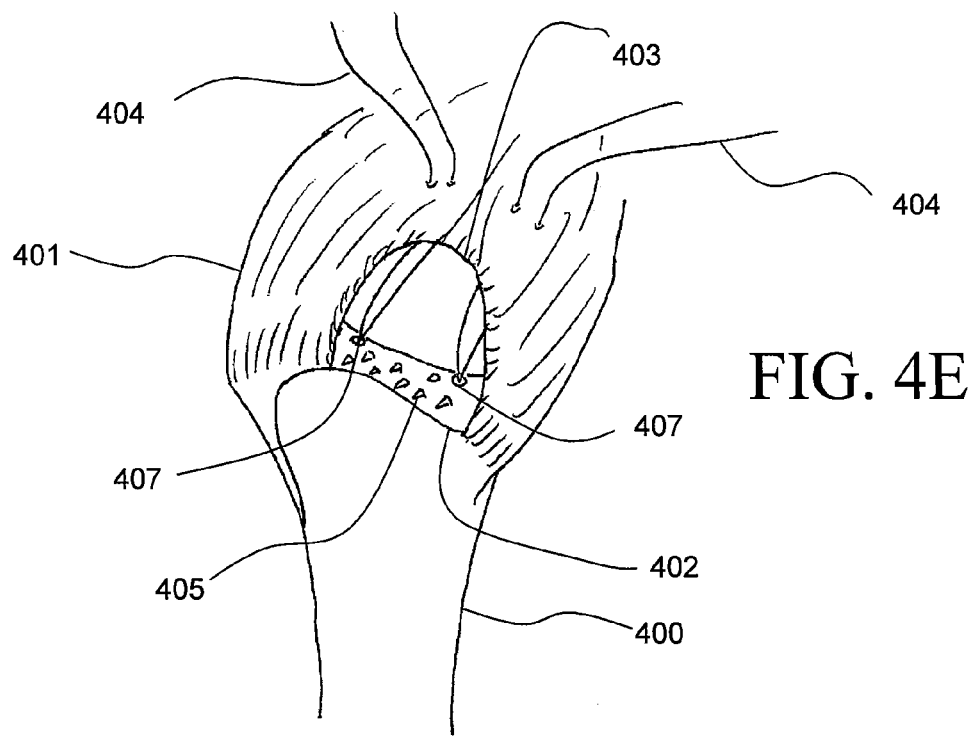
Figure 4F:
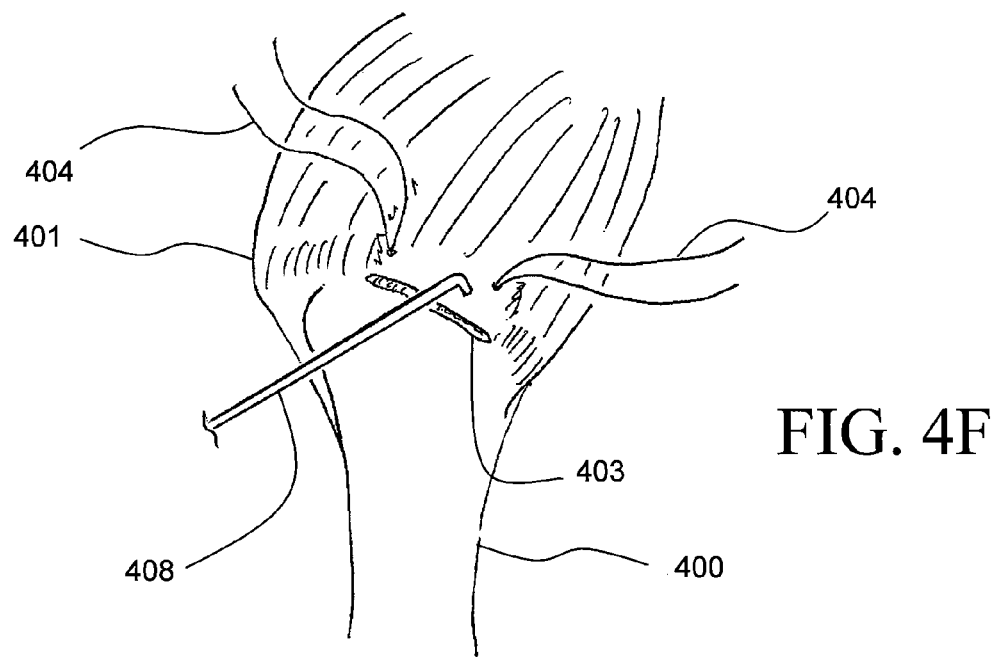
Figure 4G:
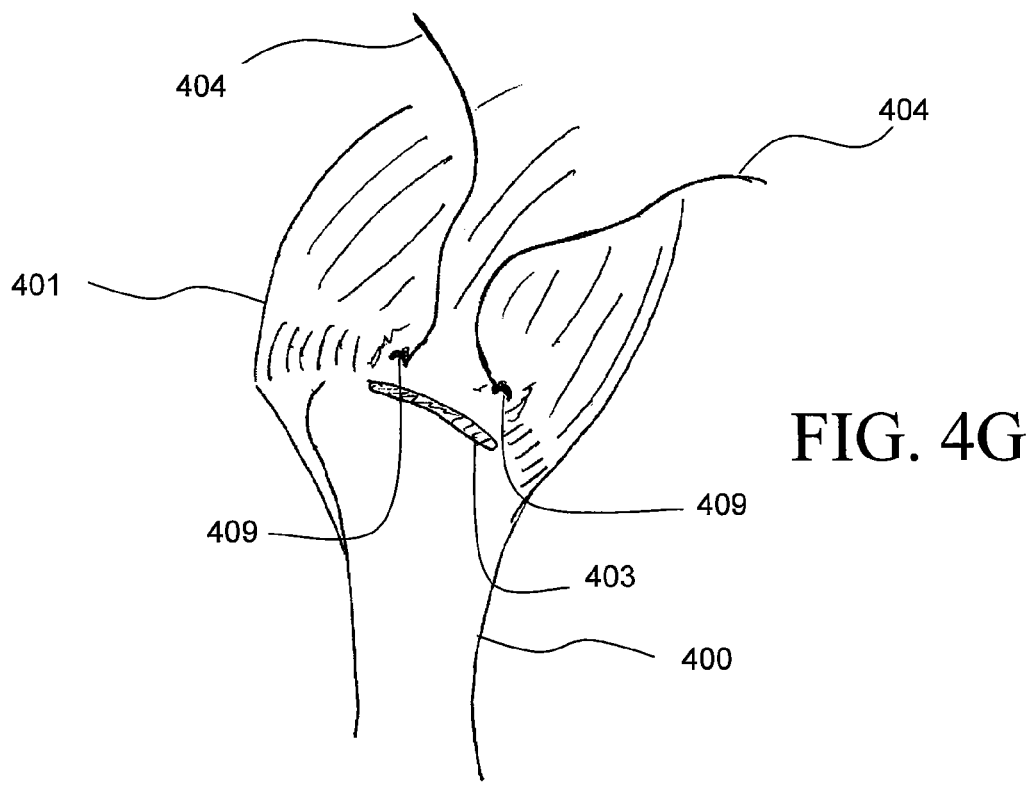
Figure 4H:
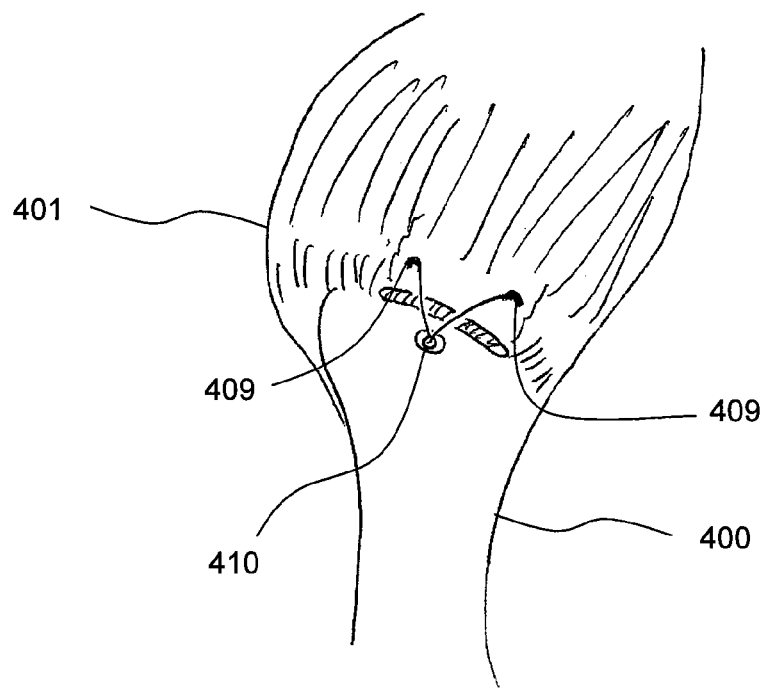

One application of the invention is to facilitate or augment tendon to bone fixation in surgical rotator cuff repair. FIG. 4A illustrates an intact rotator cuff 401 that is attached to the tuberosity of the humeral bone 400. The rotator cuff is connected to four muscles, the supraspinatus, infraspinatus, subscapularis and teres minor. These muscles act to stabilize the humeral head in the glenoid. FIG. 4B depicts a rotator cuff with a crescent-shaped tear 403, the footprint of the greater tuberosity 402, the rotator cuff tendon 401, and humeral bone 400. In rotator cuff repair, the desired outcome is to stably reattach the separated tendon to its natural point footprint on the humerus. In this example, the footprint is located on the greater tuberosity 402. FIGS. 4C-4H illustrate one example of a rotator cuff repair that utilizes the current invention. Referring to FIG. 4C, after standard preparation of the bone, one or more directional anchors 405 are placed into the bone with a delivery system 406 that is configured for either arthroscopic or open surgical delivery of the directional anchors. In arthroscopic repair, the angle of insertion of the directional anchors 405 can be controlled by manipulation of the humeral bone 400 using techniques that are well known by orthopedic surgeons. The number of directional anchors placed may depend on a variety of clinical factors such as size of the cuff tear, shape of the cuff tear, condition of the bone and tendon, as well the age and activity level of the patient. As shown in FIG. 4D, once the desired number of directional anchors are placed, standard or suture anchors 407 with pre-loaded sutures 404 that are commonly available are inserted into the greater tuberosity 402. A combination suture anchor and directional anchor 405 as described herein could also be used. The optimal location and angle of placement of the suture anchors will depend on various factors, as described above. In general, although not a requirement, a even distribution of the directional anchors with placement angles $\ominus$ ranging from 15° to 87° from the surface of the bone would be desirable to allow for even load distribution as well as positive tissue to directional anchors engagement. Referring to FIG. 4E, the sutures 404 are sutured through the tendon a distance medially to the tear 403 that will be sufficient to provide enough tendon to cover the greater tuberosity 402. Tension is then applied to sutures 404 to pull the tendon laterally over the area of the greater tuberosity 402 where the directional anchors 405 have been inserted as shown in FIG. 4F. The objective is to cover the directional anchors with the tendon over the natural footprint. Once proper tendon position is confirmed, if necessary, a suitable tool such as a arthroscopic probe 408 can be used to push the tendon onto the directional anchors and to insure that there is good contact between the tendon and the bone. Any of the directional anchors shown in FIGS. 1A-1H can be used as directional anchors 405 to penetrate or pierce the tendon as the tendon is pushed or compressed onto the directional anchors. Importantly, the directional anchors penetrate only the surface of the tendon that mates with the bone so that the directional anchors do not extend all the way through the tendon where the sharp points might cause injury to surrounding tissue. FIG. 4G illustrates the repair construct after mattress style knots 409 have been tied to appose the tendon 401 to the bone 400. In this example, as shown in FIG. 4H, one end of each suture 404 is intentionally left intact to allow fixation to the humeral bone 400 laterally of the rotator cuff tear 403 using another suture anchor 410 that is commonly available. Although not a necessary step, the extension of the suture over the edge of the rotator cuff tear to a lateral fixation point further stabilizes the rotator cuff tendon to the directional anchors 405 inserted. As can be seen by these illustrations, the sizes of the directional anchors 405 were such that they did not puncture completely through the tendon. Although not a necessary element of this invention, this embodiment allows for improving the stability of the tendon without the need for additional structures on the bursal side of the tendon, which may interfere with adjacent structures. Another embodiment of the current invention would be to first insert the directional anchors 405 through the tendon then into bone, where the tendon already has been repaired with a standard technique using sutures. The directional anchors shown in FIG. 1G and FIG. 1H and described above would work well in this embodiment of the invention as the secondary shape of the tissue-engaging element 110 would be configured to curl back into the tendon once released from the delivery system thereby pulling the tendon onto the bone.

Still with reference to FIGS. 4A-4H, one typical repair of the rotator cuff includes reattaching a tendon to its natural footprint on the humerus. By way of example only, such tendons may range from 3 mm to 5 mm in thickness T, have a footprint on the bone length of approximately 15 mm, and a width of approximately 25 mm. In this example, the thickness T of 3 mm to 5 mm can vary depending upon the individual, especially the age where a younger person may have a thicker tendon, while an older person may have a thinner less flexible tendon. The directional anchors 405 referred to above (which can have any configuration as shown in FIGS. 1A-1H), typically can have an overall length of approximately 8 mm to 24 mm. The tissue-engaging element 101 (see FIG. 1B for example) has a length L that typically ranges from 0.5 mm to approximately 4 mm long, depending upon the application. In a preferred embodiment of the present invention, the tissue-engaging element 101 has a length L that is shorter than the thickness T of a typical tendon. In other words, it is intended that with one embodiment of the present invention, the tissue-engaging element penetrates only one surface of the tendon, and does not extend all the way through the thickness T of the tendon. Further, in order to minimize any trauma to the bone in which the directional anchors 405 are inserted, the anchors have a diameter of approximately 0.5 mm to approximately 2.0 mm. It is important to reduce the diameter of the directional anchors 405 to as small as possible, while still accomplishing the intended repair procedure since the area upon which the directional anchors are inserted is a relatively small area. Stated another way, only so many anchors can be inserted in the limited space occupied by the tendon and the repair area on the humerus and bone.

Figure 5A:
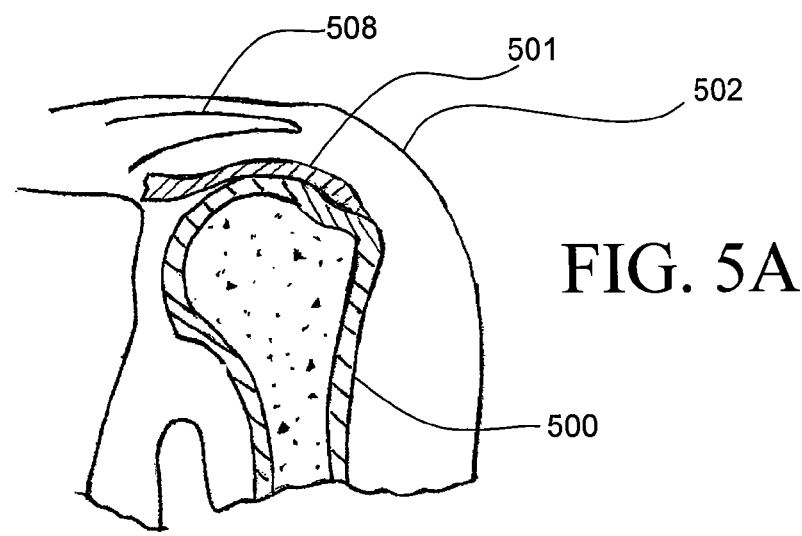
FIGS. 5A-5H depict, in cross sectional view, the various steps of repairing a rotator cuff tendon with discrete tissue to bone directional anchors using the same method depicted in FIGS. 4A-4H.
Figure 5B:
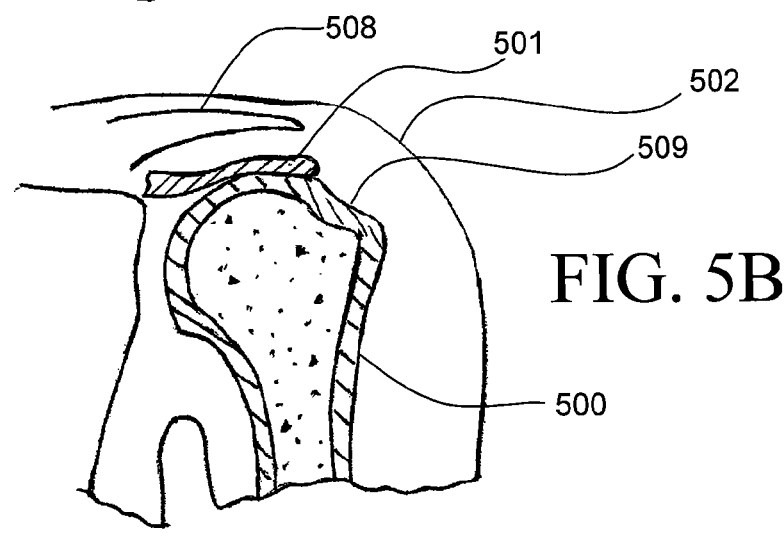
Figure 5C:
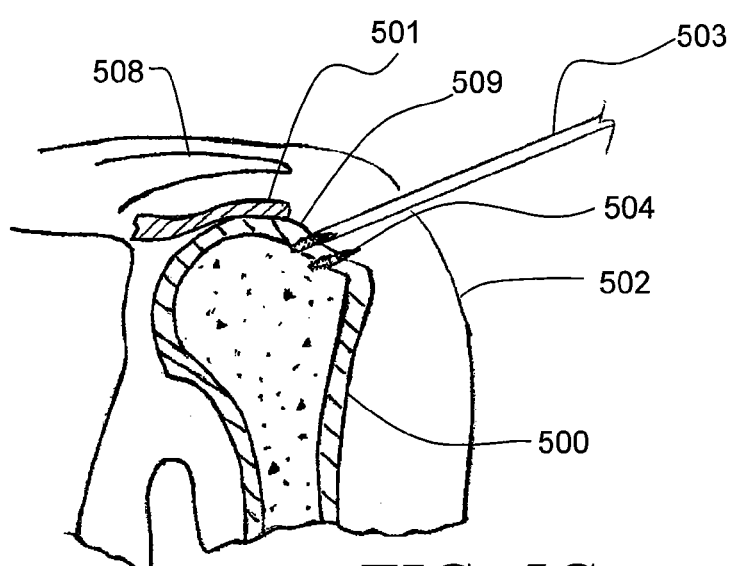
Figure 5D:
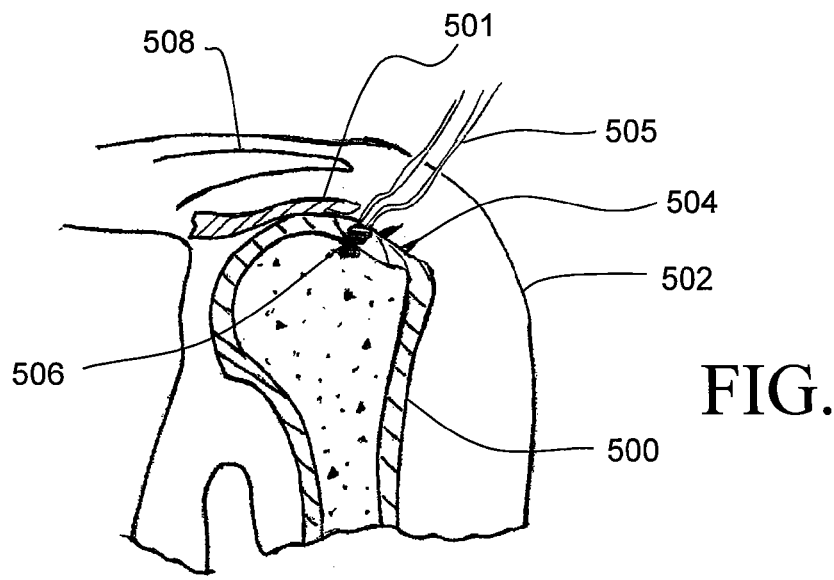

FIGS. 5A-5G are cross-sectional views illustrating the steps used to repair a rotator cuff with one embodiment of the current invention. FIG. 5A is a cross sectional view of a shoulder 502 with humeral bone 500 with an attached and un-torn rotator cuff 501 and acromium 508. FIG. 5B depicts the same shoulder as in FIG. 5A, but with rotator cuff 501 that has separated from the greater tuberosity 509. As shown in FIG. 5C, one method of repairing the rotator cuff with one embodiment of the current invention would begin with insertion of one or more directional anchors 504 with delivery system 503 into the greater tuberosity 509. As described herein the number and the location of the directional anchors placed may depend on a variety of clinical factors such as size of the cuff tear, shape of the cuff tear, condition of the bone and tendon as well the age and activity level of the patient. Placement of the rigid directional anchors at an angle $\ominus$ (between 15° and 87°) (see FIG. 5H) such that they point in a direction opposite the direction of loads on the tendon will facilitate more positive engagement and increase apposition pressure as the loads on the tendon increase. Thus, the very loads that tend to disrupt stability and cause oscillation with repairs made with suture alone will now improve contact pressure and engagement between the tendon and bone. FIG.

Figure 5E:
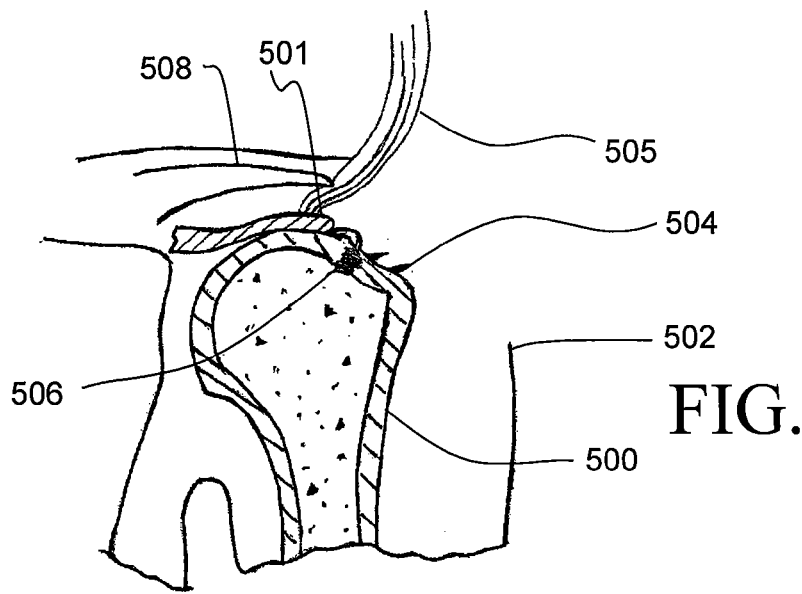
Figure 5F:
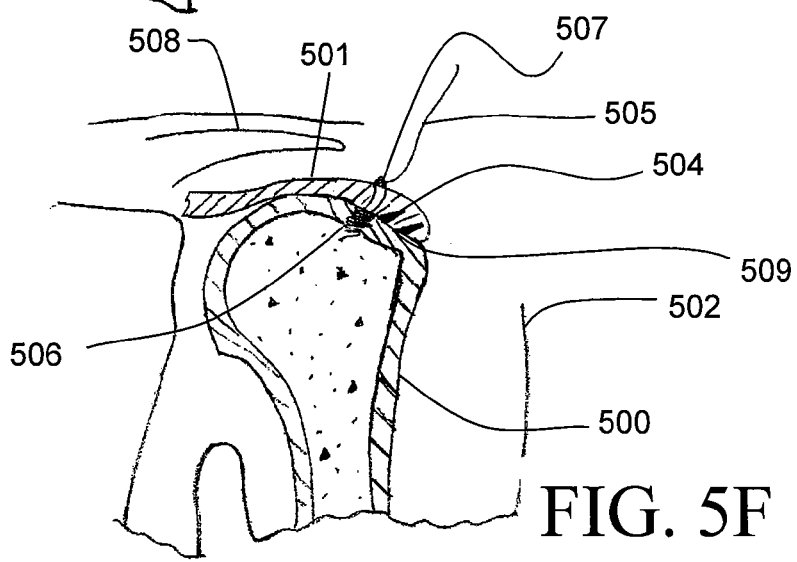
Figure 5G:
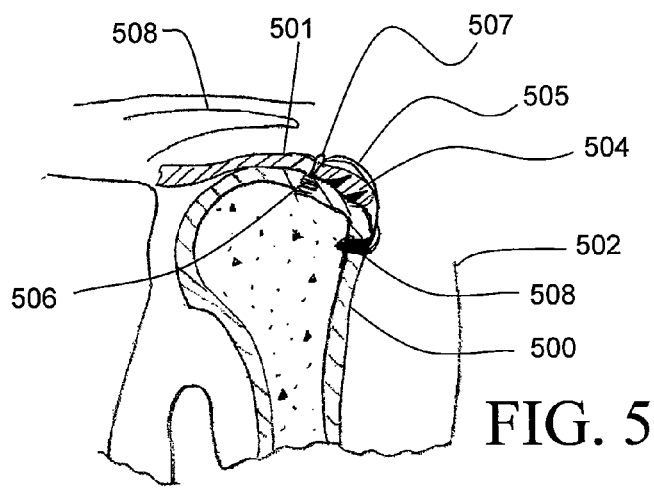
Figure 5H:
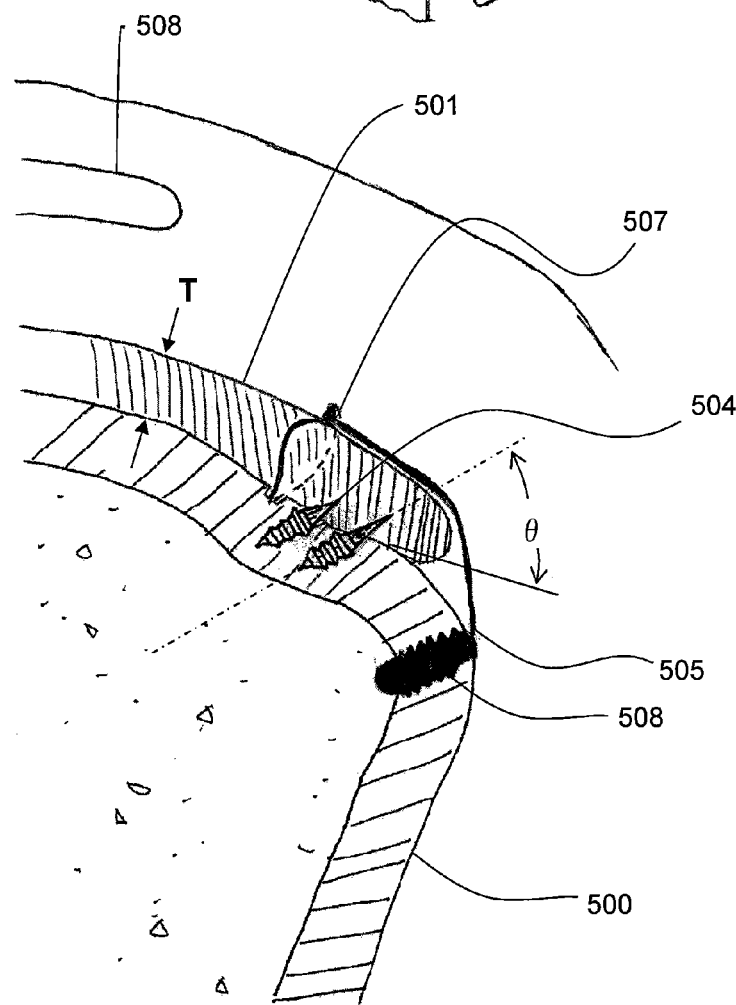

5D illustrates the next step of inserting one or more suture anchors 506 with attached sutures 505 into the humeral bone at a location deemed optimal by the surgeon. A combination suture anchor and directional anchor as described herein could also be used in place of the standard suture anchors. The sutures 505 are then sutured through the rotator cuff tendon 501 as described previously at a location medial to the lateral aspect of the rotator cuff tear as shown in FIG. 5E. FIG. 5F illustrates the following steps of positioning the tendon over the directional anchors 504 and tying of mattress style knots 507 to appose the tendon 501 to the greater tuberosity 509. As shown in FIG. 5G, and in greater detail in FIG. 5H, the ends of the sutures 505 are fixed to the humeral bone 500 at a position lateral to the lateral margin of the rotator cuff tendon 501 with an additional suture anchor 508, thus further constraining the tendon to remain connected to the directional anchors 504. The illustration in FIG. 5H clearly shows how the tendon is constrained between the directional anchors and the suture. The suture functions to hold the tendon against the directional anchors and the directional anchors, being rigid and engaged with the tendon, resist slippage of the tendon along the bone. It can also be appreciated that the directional anchors do not necessarily add profile to the overall repair. The profile of the repair is an important factor. Any implanted materials on the bursal side of the tendon in rotator cuff repair may interfere with adjacent structures as the shoulder articulates. It can also be appreciated that keeping the directional anchors exposure to the minimum required for good engagement with the tendon will minimize the potential for adverse effects should the tendon ever detach from the repair construct. Another benefit of the current invention is that much of the load carried by suture with standard suture-only repairs are now distributed amongst the directional anchors, thereby reducing the loads on the suture and minimizing the potential for suture failure and suture migration through the tendon.

It may be desired to reduce the likelihood of the development of fibrotic tissue around the directional anchors which may increase stiffness in the tendon. Certain drugs such as steroids, have been found to inhibit cell growth leading to scar tissue or fibrotic tissue growth. Examples of therapeutic drugs or pharmacologic compounds that may be loaded onto the directional anchors or into a polymeric coating on the anchors or infused into the area surrounding the anchors include steroids, taxol, aspirin, prostaglandins, and the like. Various therapeutic agents such as antithrombogenic or antiproliferative drugs are used to further control scar tissue formation. Examples of therapeutic agents or drugs that are suitable for use in accordance with the present invention include 17-beta estradiol, sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, MASS.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone. It may also be desirable to incorporate osteogenic or angiogenic factors with the directional anchors to promote bone to tendon healing.

Although the invention has been described herein with specific reference to a preferred embodiment thereof, it will be appreciated b those skilled in the art that various modifications, deletions and alterations may be made to such preferred embodiments without departing from the spirit and scope of the invention.

We claim:

1. A method for reattaching a soft tissue to bone at a natural footprint of the soft tissue on the bone, comprising:
   providing at least one directional anchor having a soft tissue anchoring section and a bone anchoring section;
   inserting the at least one directional anchor into the surface of bone so that the bone anchoring section penetrates the bone surface and the soft tissue anchoring section extends away from the bone;
   placing soft tissue over the soft tissue anchoring section so that the soft tissue anchoring section penetrates only one surface of the soft tissue; and
   applying force onto the soft tissue so that the soft tissue anchoring section extends into the soft tissue and enhances the mating engagement of the soft tissue to the bone, wherein the mating engagement is at the natural footprint of the soft tissue on the bone.

2. The method of claim 1, wherein the at least one directional anchor has a longitudinal axis and the at least one directional anchor is inserted into the bone at an angle, which is the angle between the surface of the bone and the longitudinal axis.

3. The method of claim 2, wherein the at least one directional anchor is inserted into the bone at an angle θ relative to a surface of the bone in a range of about 15° to about 87°.

4. The method of claim 3, wherein the tissue experiences at least one directional forces F tending to pull the tissue away from the bone, and wherein the directional anchor is angled in a direction substantially away from directional forces F on the tissue, thereby pulling the tissue onto the bone.

5. The method of claim 4, wherein a plurality of directional anchors are inserted into bone in a pattern corresponding to the surface of the tissue through which the tissue anchoring sections penetrate.

6. The method of claim 5, wherein the tissue anchoring sections have a length L, and the tissue has a thickness T, wherein L is less than T.

7. The method of claim 5, wherein the plurality of directional anchors are not connected to each other.

8. The method of claim 1, wherein the at least one directional anchor has an aperture for receiving a suture thread, and wherein a suture thread passes through the tissue on the side opposite the tissue anchoring section.

9. The method of claim 1, wherein the tissue engaging section does not engage the surface of the bone.

10. The method of claim 1, wherein the tissue being reattached to bone is the rotator cuff tendon, and wherein a plurality of directional anchors are inserted into bone in substantial alignment along the length of the rotator cuff tendon.

11. The method of claim 1, wherein a suture is passed along the tissue on the side of the tissue opposite the tissue engaging section to stabilize the tissue to the tissue engaging section.

12. The method of claim 1, wherein the tissue is the rotator cuff tendon which defines a footprint where the tendon mates with bone, further comprising inserting a plurality of directional anchors into the area of the footprint.

13. A method for reattaching a tissue to bone, comprising:
providing a first directional anchor, a second directional anchor, up to an Nth directional anchor, the directional anchors having a tissue anchoring section and a bone anchoring section;
preparing the surface of the bone by abrading a cortical surface of the bone;
inserting the directional anchors into the prepared cortical surface of bone so that the bone anchoring sections penetrate the prepared cortical bone surface and the tissue anchoring sections extend away from the bone;
placing tissue over the tissue anchoring sections so that the tissue anchoring sections penetrate only one surface of the tissue; and
applying force onto the tissue so that the tissue anchoring sections extend into the tissue thereby enhancing the mating engagement of the tissue to the bone.

14. The method of claim 13, wherein the directional anchors have a longitudinal axis and the directional anchors are inserted into the bone at an angle θ which is the angle between the surface of the bone and the longitudinal axis.

15. The method of claim 14, wherein the directional anchors are inserted into the bone at an angle θ relative to a surface of the bone in a range of about 15° to about 87°.

16. The method of claim 13, wherein the tissue experiences at least one directional force F tending to pull the tissue away from the bone, and wherein the directional anchors are angled in a direction substantially away from directional forces F on the tissue, thereby pulling the tissue onto the bone.

17. The method of claim 13, wherein the tissue anchoring sections have a length L, and the tissue has a thickness T, wherein L is less than T.

18. The method of claim 13, wherein the directional anchors are spaced apart.

19. The method of claim 13, wherein the at least one directional anchor has an aperture for receiving a suture thread, and wherein a suture thread passes through the tissue on the side opposite the tissue anchoring section.

20. The method of claim 13, wherein the directional anchors are inserted into the bone a predetermined distance so that the tissue engaging sections do not contact the surface of the bone.

21. A method for attaching tissue to bone, comprising:
providing a plurality of directional anchors each having a tissue anchoring section and a bone anchoring section;
preparing the surface of the bone by abrading a cortical surface of the bone;
inserting the directional anchors into the prepared cortical surface of bone so that the bone anchoring sections penetrate the prepared cortical surface of the bone and the tissue anchoring sections penetrate tissue;
placing tissue over the tissue anchoring sections so that the tissue anchoring sections penetrate only one surface of the tissue;
one of the directional anchors having an aperture for receiving a suture; and
inserting a suture thread into the tissue and through the aperture and tensioning the suture thread to secure the tissue onto the directional anchors.

22. The method of claim 21, wherein the suture is inserted into the side of the tissue opposite of the tissue engaging sections.

23. The method of claim 22, wherein the tissue is the rotator cuff tendon which defines a footprint where the tendon mates with bone, further comprising inserting the directional anchors into the area of the footprint and inserting the suture anchor into bone outside the area of the footprint.

* * * * *

UNITED STATES PATENT AND TRADEMARK OFFICE
CERTIFICATE OF CORRECTION

PATENT NO.          : 8,597,336 B2
APPLICATION NO.     : 11/966137
DATED               : December 3, 2013
INVENTOR(S)         : Erik Van Der Burg and Nathaniel Cohen It is certified that error appears in the above-identified patent and that said Letters Patent is hereby corrected as shown below:

In the Claims

Col. 10, Claim 1, line 32 – delete the word "a" between the words "reattaching" and "soft"

Col. 10, Claim 4, line 57 – change the word "forces" to "force"

Col. 11, Claim 13, line 21 – delete the word "a" between the words "reattaching" and "tissue"

Col. 12, Claim 20, line 14 – insert the word --at-- between the words "bone" and "a"

Signed and Sealed this
Eighteenth Day of August, 2015

Michelle K. Lee
*Director of the United States Patent and Trademark Office*